United States Patent
Petri et al.

(10) Patent No.: US 6,436,342 B1
(45) Date of Patent: Aug. 20, 2002

(54) SPRAYABLE DISINFECTING COMPOSITIONS AND PROCESSES FOR DISINFECTING SURFACES THEREWITH

(75) Inventors: Marco Petri, Angera Varese; Marina Trani, Rome, both of (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/308,063

(22) PCT Filed: Nov. 6, 1997

(86) PCT No.: PCT/US97/20319

§ 371 (c)(1),
(2), (4) Date: May 13, 1999

(87) PCT Pub. No.: WO98/20735

PCT Pub. Date: May 22, 1998

(30) Foreign Application Priority Data

Nov. 13, 1996 (EP) ............................................. 96870143

(51) Int. Cl.⁷ ........................... A61L 2/18; A01N 65/00; A61K 33/40
(52) U.S. Cl. .......................... 422/28; 424/405; 424/616; 424/725; 424/736; 424/739; 424/742; 424/747; 424/750; 424/765; 424/770
(58) Field of Search ............................ 422/28; 424/616, 424/725, 736, 739, 742, 747, 750, 765, 770, 405

(56) References Cited

U.S. PATENT DOCUMENTS

| 4,477,438 A | * | 10/1984 | Willcockson |
| 4,900,721 A | * | 2/1990 | Bansemir et al. |
| 5,190,749 A | | 3/1993 | Login et al. ............. 424/78.24 |
| 5,368,749 A | * | 11/1994 | La Zonby |
| 5,451,346 A | * | 9/1995 | Amou et al. |
| 5,656,302 A | | 8/1997 | Cosentino et al. .......... 424/616 |

FOREIGN PATENT DOCUMENTS

EP       667392 A2 * 8/1995

* cited by examiner

Primary Examiner—Elizabeth McKane
(74) Attorney, Agent, or Firm—Thibault Fayette

(57) ABSTRACT

The present invention relates to the disinfection of surfaces with a liquid disinfecting composition including hydrogen peroxide, an antimicrobial essential oil, and a surfactant system.

19 Claims, No Drawings

SPRAYABLE DISINFECTING COMPOSITIONS AND PROCESSES FOR DISINFECTING SURFACES THEREWITH

TECHNICAL FIELD

The present invention relates to sprayable liquid compositions suitable for disinfecting animate surfaces, for example, human skin or inanimate surfaces including hard surfaces, walls, tiles, table tops, bathroom surfaces, kitchen surfaces, as well as fabrics, clothes, carpets.

BACKGROUND

Antimicrobial compositions include materials which have the ability to disinfect. It is generally recognised that a disinfecting material greatly reduces or even eliminates the microorganisms existing on a surface. Compositions based on halogen containing compounds like hypochlorite, or on quaternary compounds, have been extensively described in the art for disinfecting purpose. Compositions comprising peroxygen bleaches are also known as disinfecting compositions.

Representative of the prior art is, for example, WO88/00795 which discloses liquid disinfecting compositions comprising a compound selected from the group of organic acids, perborates, peracids and their salts, together with other antimicrobial compounds like a quaternary ammonium salt and an essential oil.

However, such disinfecting compositions are not fully satisfactory for the consumer who is looking for an effective disinfecting composition which can be easily used in various disinfecting applications, for example, in a spray form, in a safe manner to the consumer and the environment.

Indeed, a drawback associated to such disinfecting compositions based on, for example, peracids is that they may damage surfaces onto which they are contacted to perform their disinfecting action. Indeed, such disinfecting compositions based on peracids are perceived by the consumers as being not safe to various surfaces, including hard-surfaces or fabrics.

It is therefore an object of the present invention to provide effective disinfecting compositions even when used upon high diluted conditions which are convenient to use by the consumer and safe to the surface and the environment.

It has now been found that this can be achieved by providing a sprayable liquid disinfecting composition comprising a hydrogen peroxide, an antimicrobial essential oil, and a shear thinning polymeric thickener. More particularly, it has been found that the liquid hydrogen peroxide-containing compositions of the present invention comprising said antimicrobial essential oil and shear thinning polymeric thickener, exhibit improved safety to the surface treated therewith, while providing effective disinfecting performance on clean surfaces, i.e., surfaces being free of any organic and/or inorganic soils, even at high dilution levels, i.e., up to dilution levels of 1:100 (composition:water).

Furthermore, it has been found that the sprayable liquid hydrogen peroxide-containing compositions of the present invention comprising said antimicrobial essential oil and shear thinning polymeric thickener, exhibit improved safety to the user upon usage, as compared to the same compositions without said shear thinning polymeric thickener. Indeed, an advantage of the liquid compositions of the present invention is that the inhalation by the user of said compositions is prevented or diminished, when dispensing said compositions onto a surface to be disinfected via a spray-type dispenser. Thus, the compositions herein allow to avoid potential health issues like nose and/or throat irritation and/or coughing or even lung damage, that may otherwise occur from inhalation of hydrogen peroxide mist or fog that may have formed when spraying onto a surface a hydrogen peroxide-containing composition being free of said shear thinning polymeric thickener. A further advantage of the present invention is that also eye irritation and/or damage is prevented when spraying onto a surface to be disinfected a liquid composition according to the present invention.

Another advantage of the present invention is that the liquid compositions comprising hydrogen peroxide, an antimicrobial essential oil and a shear thinning polymeric thickener are easily dispensed onto the surface to be disinfected via a spray-type dispenser (e.g., a manually operated trigger-type dispenser). Indeed, said compositions result in a shear thinning behaviour for ease of dispensing, i.e. said compositions are thinner at higher shear rates. Thus, said compositions pass easily through the pumping mechanism of a spray-type dispenser where the shear rate is high and immediately after recover their thickened character when reaching the surface to be treated and adhere thereto. Also, the life time of a spray-type dispenser head is extended, i.e., the shear thinning behaviour of said compositions prevents clogging of said head.

Another advantage of the present invention is that sprayable liquid disinfecting compositions may be applied uniformly to a relatively large area of a surface to be disinfected via a spray-type dispenser, thereby ensuring effective disinfecting performance. Indeed, effective disinfecting performance is provided on a broad range of pure bacterial strains including Gram positive and Gram negative bacterial strains and more resistant micro-organisms like fungi.

A further advantage of the compositions of the present invention is that besides the disinfecting properties delivered, good cleaning is also provided, especially in the embodiment of the present invention where the compositions herein further comprise a surfactant or a mixture thereof.

Also, the compositions according to the present invention are suitable to be used on all types of surfaces including animate surfaces like human skin or mouth (e.g., as an oral preparation or toothpaste) as well as inanimate surfaces like hard-surfaces and in laundry applications, e.g., as a laundry detergent, laundry additive or even laundry pretreater. More particularly, an advantage of the compositions according to the present invention is that they are suitable to be used on delicate surfaces including those surfaces in contact with food and/or babies in a safe manner. Furthermore, when using the compositions according to the present invention in diluted conditions, the amount of chemical residues left onto the surfaces is reduced. Thus, it may not be necessary to rinse, for example, a hard-surface after said compositions have been applied thereto in diluted conditions.

SUMMARY OF THE INVENTION

The present invention encompasses a sprayable liquid disinfecting composition comprising hydrogen peroxide, an antimicrobial essential oil and a shear thinning polymeric thickener.

The present invention further encompasses a process for disinfecting a surface wherein a liquid composition as described herein, is sprayed onto said surface.

The present invention also encompasses a liquid disinfecting composition as described herein, packaged in a spray dispenser.

DETAILED DESCRIPTION OF THE INVENTION

The Sprayable Liquid Disinfecting Compositions

As an essential element the compositions according to the present invention comprise hydrogen peroxide.

It is believed that the presence of hydrogen peroxide, in the compositions of the present invention contribute to the disinfecting properties of said compositions. Indeed, hydrogen peroxide may attack the vital function of the microorganism cells, for example, it may inhibit the assembling of ribosomes units within the cytoplasm of the microorganism cells. Also, hydrogen peroxide, is a strong oxidiser that generates hydroxyl free radicals which attack proteins and nucleic acids. Furthermore, the presence of hydrogen peroxide provides strong stain removal benefits which are particularly noticeable, for example, in laundry and/or hard surfaces applications.

Typically, the compositions herein comprise from 0.01% to 15% by weight of the total composition of hydrogen peroxide, preferably from 0.5% to 10%, and more preferably from 0.8% to 8%.

As a second essential ingredient, the compositions according to the present invention comprise an antimicrobial essential oil, or a mixture thereof. Typically, the compositions herein comprise at least 0.001% by weight of the total composition of said antimicrobial essential oil, or mixture s thereof, preferably from 0.006% to 10%, more preferably from 0.02% to 4% and most preferably from 0.04% to 2%.

Suitable antimicrobial essential oils to be used in the compositions herein are those essential oils which exhibit antimicrobial activity. It is speculated that said antimicrobial essential oils act as proteins denaturing agents. Also said antimicrobial oils are compounds of natural origin which contribute to the safety profile of the compositions of the present invention when used to disinfect any surface. A further advantage of said antimicrobial essential oils is that they impart pleasant odor tog the disinfecting compositions of the present invention without the need o f adding a perfume. Indeed, the disinfecting compositions according to the present invention deliver not only excellent disinfecting properties on clean surfaces to be disinfected but also good scent while being safe to the surfaces.

Suitable antimicrobial essential oils to be used herein include, but are not limited to, the oils obtained from thyme, lemongrass, citrus, lemons, oranges, anise, clove, aniseed, cinnamon, geranium, roses, mint, peppermint, lavender, citronella, eucalyptus, peppermint, camphor, sandalwood, cedar, rosmarin, pine, vervain fleagrass, lemongrass, ratanhiae and mixtures thereof. Particularly preferred to be used herein are eucalyptus oil, thyme oil, clove oil, cinnamon oil, geranium oil, eucalyptus oil, peppermint oil, mint oil and mixtures thereof.

As a third essential ingredient, the compositions according to the present invention comprise a shear thinning polymeric thickener or a mixture thereof. By "shear thinning polymeric thickener" it is meant herein a polymer that can be dissolved or dispersed in a water-based product, and once it is dissolved or dispersed is capable of thickening said product, said product having different viscosities upon different shears. In other words, due to the presence of said polymer the higher the shear, the less viscous the product.

These shear thinning polymeric thickeners perform a dual function when they are incorporated in the liquid compositions according to the present invention, said function being not only to prevent or diminish inhalation by the user of such a liquid composition when it is sprayed onto the surface to be disinfected, but also to provide increased contact time of the composition on vertical surfaces, thereby reducing the risk of composition dripping.

Suitable shear thinning polymeric thickeners to be used herein include synthetic and natural occurring polymers. Suitable shear thinning polymeric thickeners for used herein include polyurethane polymers, polyacrylamide polymers, polycarboxylate polymers such as polyacrylic acids and sodium salts thereof, xanthan gum or derivatives thereof, alginate or a derivative thereof, polysaccharide polymers such as substituted cellulose materials like ethoxylated cellulose, carboxymethylcellulose, hydroxymethylcellulose, hydroxypropyl cellulose, hydroxyethyl cellulose and mixtures thereof.

Preferred shear thinning polymeric thickeners for use in the compositions of the invention are xanthan gum or derivatives thereof sold by the Kelco Division of Merck under the tradenames KELTROL®, KELZAN AR®, KELZAN D35®, KELZAN S®, KELZAN XZ® and the like.

Xanthan gum is an extra cellular polysaccharide of xanthomonas campestras. Xanthan gum is made by fermentation based on corn sugar or other corn sweetener by-products. Xanthan gum comprises a poly beta-(1→4)-D-Glucopyranosyl backbone chain, similar to that found in cellulose. Aqueous dispersions of xanthan gum and its derivatives exhibit remarkable Theological properties. Xanthan gum exhibits high pseudoplasticity, i.e., over a wide range of concentrations, rapid shear thinning occurs that is generally understood to be instantaneously reversible. Preferred xanthan materials include crosslinked xanthan materials. Xanthan polymers can be crosslinked with a variety of known covalent reacting crosslinking agents reactive with the hydroxyl functionality of large polysaccharide molecules and can also be crosslinked using divalent, trivalent or polyvalent metal ions. Such crosslinked xanthan gels are disclosed in U.S. Pat. No. 4,782,901, which patent is incorporated by reference herein. Suitable crosslinking agents for xanthan materials include metal cations such as Al+3, Fe+3, Sb+3, Zr+4 and other transition metals, etc. Known organic crosslinking agents can also be used. The preferred crosslinked xanthan agent of the invention is KELZAN AR®, a product of Kelco, a division of Merck Incorporated. KELZAN AR® is a crosslinked xanthan agent that provides a thixotropic composition that can produce large particle size mist or aerosol when sprayed.

Xanthan gum or derivatives thereof are physically and chemically stable in the hydrogen peroxide-containing compositions of the present invention. Such xanthan gum or derivatives thereof are also preferred due to their high water solubility, and their human and environmental safety profile.

The polycarboxylate polymers for use herein preferably have a molecular weight of from 500.000 to 4.500.000, preferably from 1.000.000 to 4.000.000. Most preferred polymers for use herein contain from 0.5% to 4% by weight of a cross-linking agent, wherein the cross-linking agent tends to interconnect linear strands of the polymers to form the resulting cross-linked products. Suitable cross-linking agents include the polyalkenyl polyethers. Polycarboxylate polymers include the polyacrylate polymers. Others monomers besides acrylic acid can be used to form these polymers including such monomers as maleic anhydride which acts as a source of additional carboxylic groups. The molecular weight per carboxylate group of monomers containing a carboxylate group typically varies from 25 to 200, preferably from 50 to 150, more preferably from 75 to 125. Further other monomers may be present in the monomeric mixture, if desired, such as ethylene and propylene which act as diluents.

Preferred polycarboxylate polymers for use herein are the polyacrylate polymers. Commercially available polymers of the polyacrylate type include those sold under the trade names Carbopol®, Acrysol® ICS-1, Polygel®, and Sokalan®. Most preferred polyacrylate polymers are the copolymer of acrylic acid and alkyl ($C_5$–$C_{10}$) acrylate, commercially available under the tradename Carbopol® 1623, Carbopol® 695 from BF Goodrich, and copolymer of acrylic acid and maleic anhydride, commercially available under the tradename Polygel® DB from 3V Chemical company. Mixtures of any of the polycarboxylate polymers, hereinbefore described, may also be used.

The compositions according to the present invention comprise from 0.005% to 10% by weight of the total composition of a shear thinning polymeric thickener, or mixtures thereof, preferably from 0.01% to 5% by weight, more preferably from 0.02% to 2% and most preferably from 0.02% to 1%.

It has now been found that a sprayable liquid composition comprising hydrogen peroxide, an antimicrobial essential oil and a shear thinning polymeric thickener exhibits improved safety on surfaces, e.g., on hard-surfaces and/or on fabrics, and effective disinfecting performance on clean surfaces, while preventing or diminishing inhalation of said composition by the user as said composition is sprayed onto the surface to treat via a spray dispenser.

Improved safety to the surface is provided with the sprayable liquid compositions of the present invention, as compared, for example, to the same compositions with a peracid instead of said hydrogen peroxide. Indeed, the color damage, e.g., change and/or decoloration, observed when treating colored fabrics with a sprayable liquid composition according to the present invention comprising hydrogen peroxide, said antimicrobial essential oil, and said shear thinning polymeric thickener is reduced, while delivering effective disinfecting performance on said fabrics, as compared to the color damage observed when using, for example, the same composition but with a peracid instead of said hydrogen peroxide. Furthermore, it has been found that the sprayable liquid hydrogen peroxide-containing compositions of the present invention comprising said antimicrobial essential oil and said shear thinning polymeric thickener, exhibit improved safety upon usage by preventing or diminishing their inhalation by the user as they are sprayed onto the surface to treat, as compared to the same compositions without said shear thinning polymeric thickener. Indeed, the incorporation of said shear thinning polymeric thickener into the sprayable compositions herein comprising hydrogen peroxide and an antimicrobial essential oil allows the formation of mist as it is sprayed onto a surface wherein the liquid droplets/particles formed are at least partially not smaller than 10 microns.

Surface safety may be evaluated on surfaces like fabrics by measuring the tensile strength of said fabrics. The tensile strength of a fabric may be measured by employing the Tensile Strength method. This method consists of measuring the tensile strength of a given fabric by stretching said fabric until it breaks. The force, expressed in Kg, necessary to break the fabric is the "Ultimate Tensile Stress" and may be measured with "The Stress-Strain INSTRON Machine".

Effective disinfecting performance is obtained with the compositions of the present inventions on a variety of microorganisms including Gram positive bacteria like *Staphylococcus aureus*, and Gram negative bacteria like *Pseudomonas aeroginosa* as well as on fungi like *Candida albicans* present on clean surfaces, i.e., any surface being substantially free of organic and/or inorganic soils, even if used in highly diluted conditions, e.g. up to a dilution level of 1:100 (composition:water).

The disinfecting properties of a composition may be measured by the bactericidal activity of said composition. A test method suitable to evaluate the bactericidal activity of a composition on clean surfaces is described in European Standard, prEN 1040, CEN/TC 216 N 78, dated November 1995 issued by the European committee for standardisation, Brussels. European Standard, prEN 1040, CEN/TC 216 N 78, specifies a test method and requirements for the minimum bactericidal activity of a disinfecting composition. The test is passed if the bacterical colonies forming units (cfu) are reduced from a $10^7$ cfu (initial level) to a $10^2$ cfu (final level after contact with the disinfecting product), i.e. a $10^5$ reduction of the viability is necessary.

The compositions according to the present invention pass this test, even if used in highly diluted conditions.

The particle size of the liquid droplets present in the breathing zone of a potential user after simulation delivery of a sprayable liquid composition according to the present invention from a trigger activated bottle may be defined by the following test method. The particle size distribution of aerosol passing by a simulated breathing zone can be determined using a model simulating consumer use conditions. The human use simulation model may be adapted from Mokler (see in particular American Industrial Hygiene Association Journal (40), 330–346, 1979). The particle size distributions of sprayable liquid compositions can be measured using Inertial Impactor devices (Andersen and Mercer impactors).

The compositions according to the present invention are liquid compositions including aqueous or non-aqueous compositions. Preferably, the liquid compositions herein are aqueous compositions having a pH as is of not more than 12, more preferably from 2 to 10, and most preferably from 3 to 9. The pH of the compositions can be adjusted by using organic or inorganic acids, or alkalinising agents.

The compositions according to the present invention are physically stable, i.e. that no phase separation occurs when stored in rapid ageing test (RAT) at 50° C. for 10 days, and/or that no phase separation occurs during freeze-thow cycles, i.e. by heating to 50° C. and cooling to 4° C. the compositions three times in 3 days.

Optional Ingredients

The compositions according to the present invention may further comprise a surfactant or mixtures thereof. Suitable surfactants to be used herein may be any surfactant known to those skilled in the art including anionic, nonionic, cationic, amphoteric and/or, zwitterionic surfactants. Surfactants contribute to the cleaning performance of a composition of the present invention. Particularly suitable anionic surfactants to be used herein include water-soluble salts or acids of the formula $ROSO_3M$ wherein R is preferably a $C_6$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethylammonium and dimethyl piperdinium cations and quaternary ammonium cations derived from alkylamines such as ethylamine, diethylamine, triethylamine, and mixtures thereof, and the like).

Other suitable anionic surfactants to be used herein include alkyl-diphenyl-ether-sulphonates and alkylcarboxylates. Other anionic surfactants can include salts (including, for example, sodium, potassium, ammonium, and substituted ammonium salts such as mono-, di- and triethanolamine salts) of soap, $C_9$–$C_{20}$ linear alkylbenzenesulfonates, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl ester sulfonates such as $C_{14\text{-}16}$ methyl ester sulfonates; acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), acyl sarcosinates, sulfates of alkylpolysaccharides such as the sulfates of alkylpolyglucoside (the nonionic nonsulfated compounds being described below), branched primary alkyl sulfates, alkyl polyethoxy carboxylates such as those of the formula $RO(CH_2CH_2O)_kCH_2COO-M^+$ wherein R is a $C_8$–$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

Preferred anionic surfactants for use in the compositions herein are the alkyl benzene sulfonates, alkyl sulfates, alkyl alkoxylated sulfates, paraffin sulfonates and mixtures thereof.

Suitable amphoteric surfactants to be used herein include amine oxides having the following formula $R_1R_2R_3NO$ wherein each of R1, R2 and R3 is independently a saturated linear or branched hydrocarbon chain of from 1 to 30 carbon atoms. Suitable amine oxides to be used according to the present invention are amine oxides having the following formula $R_1R_2R_3NO$ wherein R1 is a hydrocarbon chain of from 1 to 30 carbon atoms, preferably from 6 to 20, more preferably from 6 to 14 and most preferably from 8 to 10, and wherein R2 and R3 are independently substituted or unsubstituted, linear or branched hydrocarbon chains of from 1 to 4 carbon atoms, preferably of from 1 to 3 carbon atoms, and more preferably are methyl groups. R1 may be a saturated linear or branched hydrocarbon chain.

Preferred amine oxides for use herein are for instance natural blend C8–C10 amine oxides as well as C12–C16 amine oxides commercially available from Hoechst.

Suitable zwitterionic surfactants to be used herein contain both cationic and anionic hydrophilic groups on the same molecule at a relatively wide range of pH's. The typical cationic group is a quaternary ammonium group, although other positively charged groups like phosphonium, imidazolium and sulfonium groups can be used. The typical anionic hydrophilic groups are carboxylates and sulfonates, although other groups like sulfates, phosphonates, and the like can be used. A generic formula for some zwitterionic surfactants to be used herein is $R_1-N+(R_2)(R_3)R_4X-$ wherein $R_1$ is a hydrophobic group; $R_2$ and $R_3$ are each $C_1$–$C_4$ alkyl, hydroxy alkyl or other substituted alkyl group which can also be joined to form ring structures with the N; $R_4$ is a moiety joining the cationic nitrogen atom to the hydrophilic group and is typically an alkylene, hydroxy alkylene, or polyalkoxy group containing from 1 to 10 carbon atoms; and X is the hydrophilic group which is preferably a carboxylate or sulfonate group.

Preferred hydrophobic groups $R_1$ are alkyl groups containing from 1 to 24, preferably less than 18, more preferably less than 16 carbon atoms. The hydrophobic group can contain unsaturation and/or substituents and/or linking groups such as aryl groups, amido groups, ester groups and the like. In general, the simple alkyl groups are preferred for cost and stability reasons.

Highly preferred zwitterionic surfactants include betaine and sulphobetaine surfactants, derivatives thereof or mixtures thereof. Said betaine or sulphobetaine surfactants are preferred herein as, they help disinfection by increasing the permeability of the bacterial cell wall, thus allowing other active ingredients to enter the cell.

Furthermore, due to the mild action profile of said betaine or sulphobetaine surfactants, they are particularly suitable for the cleaning of delicate surfaces, e.g., delicate laundry or surfaces in contact with food and/or babies. Betaine and sulphobetaine surfactants are also extremely mild to the skin and/or surfaces to be treated.

Suitable betaine and sulphobetaine surfactants to be used herein are the betaine/sulphobetaine and betaine-like detergents wherein the molecule contains both basic and acidic groups which form an inner salt giving the molecule both cationic and anionic hydrophilic groups over a broad range of pH values. Some common examples of these detergents are described in U.S. Pat. Nos. 2,082,275, 2,702,279 and 2,255,082, incorporated herein by reference. Preferred betaine and sulphobetaine surfactants herein are according to the formula

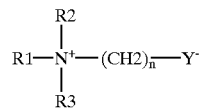

wherein R1 is a hydrocarbon chain containing from 1 to 24 carbon atoms, preferably from 8 to 18, more preferably from 12 to 14, wherein R2 and R3 are hydrocarbon chains containing from 1 to 3 carbon atoms, preferably 1 carbon atom, wherein n is an integer from 1 to 10, preferably from 1 to 6, more preferably is 1, Y is selected from the group consisting of carboxyl and sulfonyl radicals and wherein the sum of R1, R2 and R3 hydrocarbon chains is from 14 to 24 carbon atoms, or mixtures thereof.

Examples of particularly suitable betaine surfactants include C12–C18 alkyl dimethyl betaine such as coconutbetaine and C10–C16 alkyl dimethyl betaine such as laurylbetaine. Coconutbetaine is commercially available from Seppic under the trade name of Amonyl 265®. Laurylbetaine is commercially available from Albright & Wilson under the trade name Empigen BB/L®.

Other specific zwitterionic surfactants have the generic formulae:

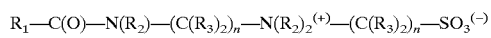

or

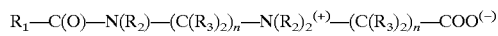

wherein each $R_1$ is a hydrocarbon, e.g. an alkyl group containing from 8 up to 20, preferably up to 18, more preferably up to 16 carbon atoms, each $R_2$ is either a hydrogen (when attached to the amido nitrogen), short chain alkyl or substituted alkyl containing from one to 4 carbon atoms, preferably groups selected from the group consisting of methyl, ethyl, propyl, hydroxy substituted ethyl or propyl and mixtures thereof, preferably methyl, each $R_3$ is selected from the group consisting of hydrogen and hydroxy groups and each n is a number from 1 to 4, preferably from 2 to 3, more preferably 3, with no more than one hydroxy group in any $(C(R_3)_2)$ moiety. The $R_1$ groups can be branched and/or unsaturated. The $R_2$ groups can also be connected to form ring structures. A surfactant of this type is a $C_{10}$–$C_{14}$ fatty acylamidopropylene(hydroxypropylene)sulfobetaine that is available from the Sherex Company under the trade name "Varion CAS sulfobetaine" ®.

In a preferred embodiment of the present invention where the compositions herein are particularly suitable for the disinfection of a hard-surface, the surfactant is typically a surfactant system comprising an amine oxide and a betaine or sulphobetaine surfactant, preferably in a weight ratio of amine oxide to betaine or sulphobetaine of 2:1 to 100:1, more preferably of 6:1 to 100:1 and most preferably 10:1 to 50:1. The use of such a surfactant system in the compositions herein suitable for disinfecting a hard-surface, provides effective cleaning performance and provides shine on the cleaned surfaces, i.e., the amount of filming/streaking left on the cleaned surface that has been treated with said compositions is minimal.

Suitable nonionic surfactants to be- used herein are fatty alcohol ethoxylates and/or propoxylates which are commercially available with a variety of fatty alcohol chain lengths and a variety of ethoxylation degrees. Indeed, the HLB values of such alkoxylated nonionic surfactants depend essentially on the chain length of the fatty alcohol, the nature of the alkoxylation and the degree of alkoxylation. Surfactant catalogues are available which list a number of surfactants, including nonionics, together with their respective HLB values.

Particularly suitable for use herein as nonionic surfactants are hydrophobic nonionic surfactants having an HLB (hydrophilic-lipophilic balance) below 16, preferably below 15, more preferably below 12, and most preferably below 10. Those hydrophobic nonionic surfactants have been found to provide good grease cutting properties.

Preferred hydrophobic nonionic surfactants to be used in the compositions according to the present invention are surfactants having an HLB below 16 and being according to the formula RO—$(C_2H_4O)_n(C_3H_6O)_mH$, wherein R is a $C_6$ to $C_{22}$ alkyl chain or a $C_6$ to $C_{28}$ alkyl benzene chain, and wherein n+m is from 0 to 20 and n is from 0 to 15 and m is from 0 to 20, preferably n+m is from 1 to 15 and, n and m are from 0.5 to 15, more preferably n+m is from 1 to 10 and, n and m are from 0 to 10. The preferred R chains for use herein are the $C_8$ to $C_{22}$ alkyl chains. Accordingly, suitable hydrophobic nonionic surfactants for use herein are Dobanol® 91-2.5 (HLB=8.1; R is a mixture of C9 and $C_{11}$ alkyl chains, n is 2.5 and m is 0), or Lutensol® TO3 (HLB=8; R is a $C_{13}$ alkyl chains, n is 3 and m is 0), or Lutensol® AO3 (HLB=8; R is a mixture of $C_{13}$ and $C_{15}$ alkyl chains, n is 3 and m is 0), or Tergitol® 25L3 (HLB= 7.7; R is in the range Of $C_{12}$ to $C_{15}$ alkyl chain length, n is 3 and m is 0), or Dobanol® 23-3 (HLB=8.1; R is a mixture of $C_{12}$ and $C_{13}$ alkyl chains, n is 3 and m is 0), or Dobanol® 23-2 (HLB=6.2; R is a mixture of $C_{12}$ and $C_{13}$ alkyl chains, n is 2 and m is 0), or Dobanol® 45-7 (HLB=11.6; R is a mixture of $C_{14}$ and $C_{15}$ alkyl chains, n is 7 and m is 0) Dobanol® 23-6.5 (HLB=11.9; R is a mixture of $C_{12}$ and $C_{13}$ alkyl chains, n is 6.5 and m is 0), or Dobanol® 25-7 (HLB=12; R is a mixture of $C_{12}$ and $C_{15}$ alkyl chains, n is 7 and m is 0), or Dobanol® 91-5 (HLB=11.6; R is a mixture of $C_9$ and $C_{11}$ alkyl chains, n is 5 and m is 0), or Dobanol® 91-6 (HLB=12.5; R is a mixture of $C_9$ and $C_{11}$ alkyl chains, n is 6 and m is 0), or Dobanol® 91-8 (HLB=13.7; R is a mixture of $C_9$ and $C_{11}$ alkyl chains, n is 8 and m is 0), Dobanol® 91-10 (HLB=14.2; R is a mixture of $C_9$ to $C_{11}$ alkyl chains, n is 10 and m is 0), or mixtures thereof. Preferred herein are Dobanol® 91-2.5, or Lutensol® TO3, or Lutensol® AO3, or Tergitol® 25L3, or Dobanol® 23-3, or Dobanol® 23-2, or mixtures thereof. These Dobanol® surfactants are commercially available from SHELL. These Lutensol® surfactants are commercially available from BASF and these Tergitol® surfactants are commercially available from UNION CARBIDE.

Other suitable surfactants also include C6–C20 conventional soaps (alkali metal salt of a C6–C20 fatty acid, preferably sodium salts).

Typically, the surfactant or mixtures thereof is present in the composition of the present invention at a level of from 0.01% to 50% by weight of the total composition, preferably from 0.01% to 30% and more preferably from 0.1% to 20%.

The compositions according to the present invention may comprise as a preferred optional ingredient further antimicrobial ingredients that contribute to the antimicrobial activity of compositions of the present invention. Such ingredients may be present up to a level of 5% by weight of the total composition, preferably from 0.001% to 1%, and include parabens like ethyl paraben, propyl paraben, methyl paraben, glutaraldehyde or mixtures thereof.

The compositions herein may further comprise a chelating agent as a preferred optional ingredient. Suitable chelating agents may be any of those known to those skilled in the art such as the ones selected from the group comprising phosphonate chelating agents, amino carboxylate chelating agents or other carboxylate chelating agents, or polyfunctionally-substituted aromatic chelating agents or mixtures thereof.

Such phosphonate chelating agents may include etidronic acid (1-hydroxyethylidene-bisphosphonic acid or HEDP) alkali metal ethane 1-hydroxy diphosphonates, as well as amino phosphonate compounds, including amino alkylene poly (alkylene phosphonate), alkali metal ethane 1-hydroxy diphosphonates, nitrilo trimethylene phosphonates, ethylene diamine tetra methylene phosphonates, and diethylene triamine penta methylene phosphonates. The phosphonate compounds may be present either in their acid form or as salts of different cations on some or all of their acid functionalities. Preferred phosphonate chelating agents to be used herein are diethylene triamine penta methylene phosphonates. Such phosphonate chelants are commercially available from Monsanto under the trade name DEQUEST®.

Polyfunctionally-substituted aromatic chelating agents may also be useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelating agent for use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987 to Hartman and Perkins. Ethylenediamine N,N'- disuccinic acid is, for instance, commercially available under the tradename ssEDDS® from Palmer Research Laboratories.

Suitable amino carboxylate chelating agents useful herein include ethylene diamine tetra acetates, diethylene triamine pentaacetates, diethylene triamine pentoacetate (DTPA), N-hydroxyethylethylenediamine triacetates, nitrilotriacetates, ethylenediamine tetrapropionates, triethylenetetraaminehexa-acetates, ethanoldiglycines, propylene diamine tetracetic acid (PDTA) and methyl glycine di-acetic acid (MGDA), both in their acid form, or in their alkali metal, ammonium, and substituted ammonium salt forms. Particularly suitable to be used herein are diethylene triamine penta acetic acid (DTPA), propylene diamine tetracetic acid (PDTA) which is, for instance, commercially available from BASF under the trade name Trilon FS® and methyl glycine di-acetic acid (MGDA).

Further carboxylate chelating agents to be used herein include malonic acid, salicylic acid, glycine, aspartic acid, glutamic acid, or mixtures thereof.

Said chelating agents, especially phosphonate chelating agents like diethylene triamine penta methylene phosphonates, are particularly preferred in the compositions according to the present invention as they have been found to further contribute to the disinfecting properties of hydrogen peroxide.

Typically, the compositions according to the present invention comprise up to 5% by weight of the total composition of a chelating agent, or mixtures thereof, preferably from 0.002% to 3% by weight and more preferably from 0.002% to 1.5%.

The compositions herein may further comprise a radical scavenger as a preferred optional ingredient. Suitable radical scavengers for use herein include the well-known substituted mono and di hydroxy benzenes and derivatives thereof, alkyl- and aryl carboxylates and mixtures thereof. Preferred radical scavengers for use herein include di-tert-butyl hydroxy toluene (BHT), p-hydroxy-toluene, hydroquinone (HQ), di-tert-butyl hydroquinone (DTBHQ), mono-tert-butyl hydroquinone (MTBHQ), tert-butyl-hydroxy anysole (BHA), p-hydroxy-anysol, benzoic acid, 2,5-dihydroxy benzoic acid, 2,5-dihydroxyterephtalic acid, toluic acid, catechol, t-butyl catechol, 4-allyl-catechol, 4-acetyl catechol, 2-methoxy-phenol, 2-ethoxy-phenol, 2-methoxy4-(2-propenyl)phenol, 3,4-dihydroxy benzaldehyde, 2,3-dihydroxy benzaldehyde, benzylamine, 1,1,3-tris(2-methyl-4-hydroxy-5-t-butylphenyl) butane, tert-butyl-hydroxy-anyline, p-hydroxy anyline as well as n-propyl-gallate. Highly preferred for use herein is di-tert-butyl hydroxy toluene, which is, for example, commercially available from SHELL under the trade name IONOL CP®. These radical scavengers further contribute to the stability of the hydrogen peroxide-containing compositions herein.

Typically, the compositions according to the present invention comprise up to 5% by weight of the total composition of a radical scavenger, or mixtures thereof, preferably from 0.01% to 1.5% by weight and more preferably from 0.01% to 1%.

The compositions herein may comprise as an optional ingredient a solvent or mixtures thereof. When used, solvents will, advantageously, give an enhanced cleaning to the compositions herein. Suitable solvents for incorporation in the compositions according to the present invention include propylene glycol derivatives such as n-butoxypropanol or n-butoxypropoxypropanol, water-soluble CARBITOL® solvents or water-soluble CELLOSOLVE® solvents. Water-soluble CARBITOL® solvents are compounds of the 2-(2-alkoxyethoxy)ethanol class wherein the alkoxy group is derived from ethyl, propyl or butyl. A preferred water-soluble carbitol is 2-(2-butoxyethoxy)ethanol also known as butyl carbitol. Water-soluble CELLOSOLVE® solvents are compounds of the 2-alkoxyethoxyethanol class, with 2-butoxyethoxyethanol being preferred. Other suitable solvents are benzyl alcohol, methanol, ethanol, isopropyl alcohol and diols such as 2-ethyl-1,3-hexanediol and 2,2,4-trimethyl-1,3-pentanediol and mixture thereof. Preferred solvents for use herein are n-butoxypropoxypropanol, butyl carbitol® and mixtures thereof. A most preferred solvent for use herein is butyl carbitol®.

The solvents may typically be present within the compositions of the invention at a level up to 10% by weight, preferably from 2% to 7% by weight of the composition.

The compositions herein may further comprise a variety of other optional ingredients such as buffers (e.g. borate buffers), builders, stabilisers, bleach activators, soil suspenders, dye transfer agents, brighteners, perfumes, anti dusting agents, enzymes, dispersant, dye transfer inhibitors, pigments, perfumes and dyes.

The compositions according to the present invention preferably have a viscosity of from 10 cps to 4000 cps, more preferably from 20 cps to 2000 cps, most preferably from 30 cps to 700 cps, when measured with a Carrimed Rheometer at a temperature of 25° C., and a shear rate of 15–35 s$^{-1}$.

Packaging Form of the Compositions

The compositions herein may be packaged in a variety of suitable detergent packaging known to those skilled in the art. The liquid compositions herein may desirably be packaged in manually operated spray dispensing containers. Accordingly, the present invention also encompasses liquid compositions of the invention packaged in a spray dispenser, preferably in a trigger spray dispenser or in a pump spray dispenser.

Indeed, said spray-type dispensers allow to uniformly apply to a relatively large area of a surface to be disinfected the liquid compositions suitable for use according to the present invention; thereby contributing to the disinfecting properties of said compositions. Such spray-type dispensers are particularly suitable to disinfect vertical surfaces.

Suitable spray-type dispensers to be used according to the present invention include manually operated foam trigger-type dispensers sold, for example, by Specialty Packaging Products, Inc. or Continental Sprayers, Inc. These types of dispensers are disclosed, for instance, in U.S. Pat. No. 4,701,311 to Dunnining et al. and U.S. Pat. No. 4,646,973 and U.S. Pat. No. 4,538,745 both to Focarracci. Particularly preferred to be used herein are spray-type dispensers such as T 8500® or T8900® commercially available from Continental Sprayers International or T 8100® commercially available from Canyon, Northern Ireland. In such a dispenser the liquid composition is divided in fine liquid droplets resulting in a spray that is directed onto the surface to be treated. Indeed, in such a spray-type dispenser the composition contained in the body of said dispenser is directed through the spray-type dispenser head via energy communicated to a pumping mechanism by the user as said user activates said pumping mechanism. More particularly, in said spray-type dispenser head the composition is forced against an obstacle, e.g. a grid or a cone or the like, thereby providing shocks to help atomise the liquid composition, i.e. to help the formation of liquid droplets.

Disinfecting Processes

The present invention encompasses a process of disinfecting a surface wherein a liquid disinfecting composition as described hereinbefore is sprayed onto a surface in its neat form.

By "surface" it is meant herein any surface including animate surface like human skin, mouth, teeth and inanimate surfaces. Inanimate surfaces include, but are not limited to, hard-surfaces typically found in houses like kitchens, bathrooms, or in car interiors, e.g., tiles, walls, floors, chrome, glass, smooth vinyl, any plastic, plastified wood, table top, sinks, cooker tops, dishes, sanitary fittings such as sinks, showers, shower curtains, wash basins, WCs and the like, as well as fabrics including clothes, curtains, drapes, bed linens, bath linens, table cloths, sleeping bags, tents, upholstered furniture and the like, and carpets. Inanimate surfaces also include household appliances including, but not limited to, refrigerators, freezers, washing machines, automatic dryers, ovens, microwave ovens, dishwashers and so on. The compositions of the present invention have been found to be particularly suitable for the disinfection of non-horizontal hard surfaces.

In the preferred embodiment of the process of the present invention wherein said liquid composition is sprayed to a hard-surface to be disinfected via a spray dispenser, it is not necessary to rinse the surface after the composition has been applied, indeed no visible residues are left onto the surface.

The present invention will be further illustrated by the following examples.

EXAMPLES

The following sprayable liquid compositions were made by mixing the listed ingredients in the listed proportions (weight % unless otherwise specified).

These compositions were packaged in bottles equipped with a trigger spray foamer T8900® commercially available from Continental Sprayers Inc.

These sprayable liquid compositions passed the prEN 1040 test of the European committee of standardisation. These sprayable compositions provide effective disinfection when used neat or diluted, e.g. at 1:100, 1:25, 1:50 dilution levels, on clean surfaces with limited damage or even no damage to said surface (e.g. color change on fabrics) while being safe to the user. These compositions, packaged in a spray dispenser, exhibit reduced inhalation of said compositions by the user as said compositions are sprayed onto a surface.

| Compositions (weight %) | I | II | III | IV | V | VI |
|---|---|---|---|---|---|---|
| Hydrogen peroxide | 2.0 | 1.0 | 1.0 | 1.0 | 2.5 | 3.0 |
| Betaine* | 1.0 | 1.0 | 0.05 | 0.5 | 0.3 | 3.0 |
| $C_{10}$ amine oxide** | 1.5 | 1.5 | 0.9 | 0.9 | 0.9 | 1.0 |
| Thyme oil | 0.05 | 0.1 | 0.05 | — | — | — |
| Geranium oil | — | — | — | 0.1 | — | — |
| Eucalyptus oil | 0.1 | — | 0.1 | — | — | — |
| Clove oil | — | — | — | — | 0.15 | 0.2 |
| HEDP | 0.1 | 0.09 | 0.09 | 0.05 | 0.2 | 0.3 |
| BHT | 0.05 | 0.05 | 0.06 | 0.1 | 0.1 | 0.15 |
| Tetraborate | 0.5 | 0.5 | 0.5 | 1.0 | 1.0 | 1.5 |
| Dobanol 91-10 ® | 0.1 | 0.05 | 0.05 | 0.5 | 0.5 | 1.0 |
| Fatty acid | — | 0.1 | 0.1 | — | — | — |
| Xanthan Gum | 0.1 | 0.05 | 0.04 | 0.03 | 0.05 | — |
| Polymer@ | — | — | — | — | — | 0.5 |
| Water and minors | up to 100% | | | | | |
| NaOH up to pH 8.5 | | | | | | |

| Compositions (weight %) | VII | VIII | IX | X |
|---|---|---|---|---|
| Hydrogen peroxide | 2.0 | 2.0 | 1.0 | 1.0 |
| Eucalyptus oil | — | — | 0.5 | — |
| Geranium oil | — | 0.5 | — | — |
| Thyme oil | 0.5 | — | — | 0.8 |
| Dobanol 91-10 ® | 2.0 | 1.0 | 1.0 | 1.0 |
| Betaine* | 1.5 | 1.5 | 1.0 | 2.0 |
| Polymer@ | 0.5 | 0.5 | — | — |
| Xanthan gum | — | — | 0.3 | 0.4 |
| Water and minors | up to 100% | | | |
| H2SO4 up to pH 4 | | | | |

Betaine* is either coconut betaine commercially available from Seppic under the trade name Amonyl 265 ® or laurylbetaine commercially available from Albright & Wilson under the trade name Empigen BB/L ® or mixtures thereof.
$C_{10}$ amine oxide** is Decyl dimethyl amine oxide.
HEDP is etidronic acid.
BHT is butylated hydroxy toluene.
Tetraborate is the sodium tetraborate decahydrate.
Dobanol 91-10 ® is a C9–C11 nonionic ethoxylated (10) surfactant.
Polymer@ is Copolymer of acrylic acid and alkyl (C5–C10) acrylate commercially available under the trade name Carbopol ® 1623 from BF Goodrich.

What is claimed is:

1. A sprayable liquid disinfecting composition comprising:
   a) at least about 0.001% by weight, of an essential oil antimicrobial agent;
   b) from about 0.01% to about 15% by weight, of hydrogen peroxide;
   c) from 0.01% to 50% by weight, a surfactant system, said surfactant system comprising:
      i) an amine oxide surfactant; and
      ii) a betaines or sulphobetaine surfactant;
         wherein the ratio of said amine oxide surfactant to betaine surfactant or sulphobetaine surfactant is from 2:1 to 100:1; and
   d) the balance carrier an d adjunct ingredients.

2. A composition according to claim 1 wherein said antimicrobial agent is an essential oil derived from a source selected from the group consisting of thyme, lemongrass, lemons, oranges, anise, cloves, aniseed, cinnamon, geraniums, roses, mint, peppermint, lavender, citronella, eucalyptus, sandalwood, cedar, rosmarin, pine, vervain fleagrass, ratanhiae, and mixtures thereof.

3. A composition according to claim 1 wherein said antimicrobial agent comprises an essential oil selected from the group consisting of eucalyptus oil, thyme oil, clove oil, cinnamon oil, geranium oil, peppermint oil, mint oil, and mixtures thereof.

4. A composition according to claim 1 wherein said antimicrobial agent comprises a terpene selected from the group consisting of eugenol, thymol, camphor, caryophillin, cinnamic aldehyde, geraniol, nerol, citronellol, menthol, and mixtures thereof.

5. A composition according to claim 1 comprising from 0.006% to 10% by weight, of an essential oil antimicrobial agent.

6. A composition according to claim 5 comprising from 0.02% to 4% by weight, of an essential oil antimicrobial agent.

7. A composition according to claim 6 comprising from 0.04% to 2% by weight, of an essential oil antimicrobial agent.

8. A composition according to claim 1 comprising from 0.5% to 10% by weight of hydrogen peroxide.

9. A composition according to claim 8 comprising from 0.8% to 8% by weight of hydrogen peroxide.

10. A composition according to claim 9 comprising from 0.01% to 30% by weight, of said surfactant system.

11. A composition according to claim 10 comprising from 0.1% to 20% by weight, of said surfactant system.

12. A composition according to claim 1 wherein said ratio of said amine oxide surfactant to betaine surfactant or sulphobetaine surfactant is from 6:1 to 100:1.

13. A composition according to claim 12 wherein said ratio of said amine oxide surfactant to betaine surfactant or sulphobetaine surfactant is from 10:1 to 50:1.

14. A composition according to claim 1 further comprising from 0.001% to 1% by weight of a paraben antimicrobial selected from the group comprising methyl paraben, ethyl paraben, propyl paraben, glutaraldehyde, and mixtures thereof.

15. A composition according to claim 1 further comprising from 0.002% to 3% by weight, of a chelating agent.

16. A composition according to claim 15 comprising from 0.002% to 1.5% by weight, of a chelating agent.

17. A sprayable liquid disinfecting composition comprising:
   a) at least about 0.001% by weight, of an essential oil antimicrobial agent, said essential oil derived from a source selected from the group consisting of thyme, lemongrass, lemons, oranges, anise, cloves, aniseed, cinnamon, geraniums, roses, mint, peppermint, lavender, citronella, eucalyptus, sandalwood, cedar, rosmarin, pine, vervain, fleagrass, ratanhiae, and mixtures thereof;
   b) from about 0.01% to about 15% by weight, of hydrogen peroxide;
   c) from 0.01% to 50% by weight, a surfactant system comprising:
      i) an amine oxide surfactant; and
      ii) a betaines or sulphobetaine surfactant;
         wherein the ratio of said amine oxide surfactant to betaine surfactant or sulphobetaine surfactant is from 2:1 to 100:1; and
   d) the balance carrier and adjunct ingredients.

18. A method for disinfecting surfaces comprising the step of contacting a surface with a composition comprising:
   a) at least about 0.001% by weight, of an essential oil antimicrobial agent;
   b) from about 0.01% to about 15% by weight, of hydrogen peroxide;
   c) from 0.01% to 50% by weight, a surfactant system, said surfactant system comprising:
      i) an amine oxide surfactant; and
      ii) a betaines or sulphobetaine surfactant;
         wherein the ratio of said amine oxide surfactant to betaine surfactant or sulphobetaine surfactant is from 2:1 to 100:1
   d) the balance carrier and adjunct ingredients.

19. A method according to claim 18 wherein said antimicrobial agent is an essential oil derived from a source selected from the group consisting of thyme, lemongrass, lemons, oranges, anise, cloves, aniseed, cinnamon, geraniums, roses, mint, peppermint, lavender, citronella, eucalyptus, sandalwood, cedar, rosmarin, pine, vervain, fleagrass, ratanhiae, and mixtures thereof.

* * * * *